United States Patent
Matsubara et al.

(10) Patent No.: US 7,238,518 B2
(45) Date of Patent: Jul. 3, 2007

(54) OLIGONUCLEOTIDE-IMMOBILIZED SUBSTRATE FOR DETECTING METHYLATION

(75) Inventors: Nagahide Matsubara, Okayama (JP); Takeshi Nagasaka, Okayama (JP); Naoki Kimura, Chiba (JP); Osamu Suzuki, Chiba (JP)

(73) Assignee: Nisshinbo Industries, Inc., Chuo-ku, Tokyo (JP)

( * ) Notice: Subject to any disclaimer, the term of this patent is extended or adjusted under 35 U.S.C. 154(b) by 346 days.

(21) Appl. No.: 10/677,853

(22) Filed: Oct. 2, 2003

(65) Prior Publication Data

US 2005/0089870 A1    Apr. 28, 2005

(30) Foreign Application Priority Data

Oct. 4, 2002    (JP) .............................. 2002-292122

(51) Int. Cl.
*C12Q 1/68* (2006.01)
*C07H 21/04* (2006.01)

(52) U.S. Cl. ............................... 435/287.2; 435/287.1; 435/6; 536/23.1; 536/24.3

(58) Field of Classification Search ..................... None
See application file for complete search history.

(56) References Cited

U.S. PATENT DOCUMENTS

| 6,936,419 B1 * | 8/2005 | Berlin ........................... 435/6 |
| 2001/0053519 A1 * | 12/2001 | Fodor et al. .................. 435/6 |
| 2003/0096289 A1 | 5/2003 | Suzuki et al. |
| 2003/0152950 A1 * | 8/2003 | Garner et al. .................. 435/6 |

FOREIGN PATENT DOCUMENTS

| EP | 1 104 687 | 6/2001 |
| WO | WO 97/46705 | 12/1997 |
| WO | WO 99/55905 | 11/1999 |
| WO | WO 00/70090 | 11/2000 |
| WO | WO 01/27317 | 4/2001 |
| WO | WO 01/38565 | * 5/2001 |
| WO | WO 01/62064 | 8/2001 |
| WO | WO 01/68911 | 9/2001 |
| WO | WO 02/77272 | 10/2002 |

OTHER PUBLICATIONS

Pao et al. (Human Molecular Genetics, vol. 10, No. 9, pp. 903-910).*
Cameron et al. (Blood, vol. 94, No. 7, pp. 2445-2451, Oct. 1999).*
Fajkusova et al. (Blood Cells, Molecules and Diseases, vol. 26, No. 3, Jun. 2000).*
Adorjan, et al. "Tumour Class Prediction and Discovery by Microarray-Based DNA Methylation Analysis," *Nucleic Acids Research*, vol. 30, No. 5, p. e21, 2002.
Model, et al. "Feature Selection for DNA Methylation Based Cancer Classification," *Bioinformatics*, Oxford University Press, Oxford, Great Britain, vol. 17, Supplement 1, pp. S157-S164, 2001.
Gitan, et al. "Methylation-Specific Oligonucleotide Microarray: A New Potential for High-Throughput Methylation Analysis," *Genome Research*, vol. 12, pp. 158-164, 2001.
Nagasaka, et al. "CpG Island Microarray to Analyze Methylation of $O^8$ Methyiguarine-DNA Methyltransferase in Colon Cancer," *Proceedings of the American Association for Cancer Research Annual Meeting*, vol. 43, p. 1129, 2002.
European Search Report, completed Mar. 3, 2004, and issued to a foreign pending application.

* cited by examiner

*Primary Examiner*—Jeanine A. Goldberg
(74) *Attorney, Agent, or Firm*—Knobbe, Martens, Olson & Bear, LLP (57) ABSTRACT

The presence or absence of methylation of C's in CpG dinucleotide in a sample DNA that contains a target sequence including the CpG dinucleotide is detected as follows. Multiple kinds of capture oligonucleotides immobilized on a base material and including: an oligonucleotide having a nucleotide sequence complimentary to or identical to a nucleotide sequence corresponding to the target sequence in which all of C's other than C's in the all of CpG dinucleotide are replaced with T's; and an oligonucleotide having a nucleotide sequence complimentary to or identical to a nucleotide sequence corresponding to the target sequence in which all of C's are replaced with T's are hybridized with the sample DNA in which non-methylated C's have been converted into U's by deamination or an amplification product thereof, and the presence or absence of methylation is detected based on the result of the hybridization.

8 Claims, 3 Drawing Sheets

Fig. 1

(SEQ ID NO: 4)

ttaaggtata gagttttagg YggaagttggEgaaggYgtYg ttYggtttgt atYggtYgaa gggttattYg

SEQ ID NO:1 SEQ ID NOS: 3, 5 ggttaggYgt atagggtagY ggYgttgtYg gaggattagg gtYggYgtgt tggYgtttag YgaggatgYg tagattgttt taggttYggY gtYgtYgtat tgggtatgYg tYgattYggt YgggYgggaa tatttYgttt

SEQ ID NOS: 6, 7

YgttYgggtt tYgttttagt ttYgttttYg YgYgtttYgg tttYgttttY gYgYgttttt ttgttttttt taggttttYg gtttYgtttY gttttagatt tYgttttaYg tYgttatttt YgtgtttttY ggtttYgttt tYgYgtttYg gatatgttgg gatagttYgY gttttagaa YgttttgYgt ttYgaYgttY gtaggttttY

SEQ ID NOS: 8, 9 SEQ ID NOS: 10, 11 gYggtgYgta tYgtttgYga tttggtgagt gtttgggtYg tttYgttttY ggaagagtgY ggagtttttt

SEQ ID NOS: 12, 13 ttYgggaYgg tggtagtttY gagtggtttt gtaggtgttg

SEQ ID NO: 4 SEQ ID NO: 2

SEQUENCE LISTING

<160> NUMBER OF SEQ ID NOS: 29

<210> SEQ ID NO 1
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 1
ggtatagagt tttaggcgga agtt                                              24

<210> SEQ ID NO 2
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 2
aaagctcacc aaaacatcca caac                                              24

<210> SEQ ID NO 3
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 3
tttcggcgga agttggga                                                     18

<210> SEQ ID NO 4
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 4
ccatcaaagc tcaccaaaac atcc                                              24

<210> SEQ ID NO 5
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 5
ttttggcgga agttggga                                                     18

<210> SEQ ID NO 6
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 6
gtcgtcgtat tgggtatg                                                     18

<210> SEQ ID NO 7
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 7
gttgttgtat tgggtatg                                              18

<210> SEQ ID NO 8
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 8
gggatagttc gcgttttta                                             19

<210> SEQ ID NO 9
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 9
gggatagttt gtgttttta                                             19

<210> SEQ ID NO 10
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 10
ttcgacgttc gtaggttttc                                            20

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
tttgatgttt gtaggttttt                                            20

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
gtttgggtcg tttcgttttc                                            20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 13
gtttgggttg ttttgttttt                                              20

<210> SEQ ID NO 14
<211> LENGTH: 530
<212> TYPE: DNA
<213> ORGANISM: Homo sapiens

<400> SEQUENCE: 14
ttaaggtata gagttttagg yggaagttgg gaaggygtyg ttyggtttgt atyggtygaa   60
gggttattyg ggttaggygt atagggtagy ggygttgtyg gaggattagg gtyggygtgt  120
tggygtttag ygaggatgyg tagattgttt taggttyggy gtygtygtat tgggtatgyg  180
tygattyggt ygggygggaa tatttygttt ygttygggtt tygttttagt ttygttttyg  240
ygygtttygg tttygtttty gygygttttt ttgttttttt taggttttyg gtttygttty  300
gttttagatt tygtttttayg tygttatttt ygtgttttty ggtttygttt tygygtttyg  360
gatatgttgg gatagttygy gttttttagaa ygttttgygt ttygaygtty gtaggttttty  420 gyggtgygta tygtttgyga tttggtgagt gtttggtyg tttygttty ggaagagtgy   480 ggagtttttt ttygggaygg tggtagttty gagtggtttt gtaggtgttg            530

<210> SEQ ID NO 15
<211> LENGTH: 25
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (17)...(17)
<223> OTHER INFORMATION: n=inosine

<400> SEQUENCE: 15
ggagtgaagg aggttanggg taagt                                        25

<210> SEQ ID NO 16
<211> LENGTH: 23
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (8)...(8)
<223> OTHER INFORMATION: n=inosine

<400> SEQUENCE: 16
ccaacctnct ctatcaccac tta                                          23

<210> SEQ ID NO 17
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 17
acgatatata acgaacgacg aacg                                         24

<210> SEQ ID NO 18
<211> LENGTH: 24
<212> TYPE: DNA
<213> ORGANISM: Artificial Sequence
```

```
<220> FEATURE:
<223> OTHER INFORMATION: synthetic oligonucleotide

<400> SEQUENCE: 18
acaatatata acaaacaaca aaca                                              24

<210> SEQ ID NO 19
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 19
ccactacgaa ctaaacacga atactacga                                         29

<210> SEQ ID NO 20
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 20
ccactacaaa ctaaacacaa atactacaa                                         29

<210> SEQ ID NO 21
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 21
ctacccgcga acgcgacgtc gaacg                                             25

<210> SEQ ID NO 22
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 22
ctacccacaa acacaacatc aaaca                                             25

<210> SEQ ID NO 23
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 23
taatctatcg ccgcctcatc gta                                               23

<210> SEQ ID NO 24
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 24
taatctatca ccacctcatc ata                                               23
```

```
<210> SEQ ID NO 25
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 25
cgtttttaaa aactcgaaaa atacg                                           25

<210> SEQ ID NO 26
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 26
catttttaaa aactcaaaaa ataca                                           25

<210> SEQ ID NO 27
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 27
cgtccctccc taaaacgact actacccg                                        28

<210> SEQ ID NO 28
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 28
catccctccc taaaacaact actaccca                                        28

<210> SEQ ID NO 29
<211> LENGTH: 900
<212> TYPE: DNA
<213> ORGANISM: Homo sapiens

<400> SEQUENCE: 29
aygagcagct ctctcttcag gagtgaagga ggttaygggc aagtygtttt gaygtagayg      60
ttttattagg gtygygygtt ygtygttygt tatatatygt tygtagtatt ygtgtttagt     120
ttygtagtgg ygttygaygt ygygttygyg ggtagttayg atgaggyggy gatagattag     180
gtatagggtt ttatygtttt tyggaggttt tattattaaa taaygttggg tttattyggg     240
tyggaaaatt agagtttygt ygattttat tttgtttttt tggygygtta tttatatttt     300
gygggaggtt ataagagtag ggttaaygtt agaaaggtyg taagggggaga ggaggagttt     360 gagaagygtt aagtattttt ttygttttgy gttagattat tttagtagag gtatataagt     420 tyggttygg tattttgtt tttattggtt ggatatttyg tattttyga gttttaaaa     480 aygaattaat aggaagagyg atagygatt tttaaygygt aaygtatat ttttttaggt     540 agygggtagt agtygttta gggagggayg aagagattta gtaatttata gagttgagaa     600
atttgattgg tatttaagtt gtttaattaa tagttgtcgt tgaagggtgg ggttggatgg     660
cgtaagttat agttgaagga agaacgtgag tacgaggtat tgaggtgatt ggttgaaggt     720
```

| | | | | |
|---|---|---|---|---|
| attttcgttg | agtatttaga | cgttttttg | gttttttggg | cgttaaaatg tcgttcgtgg | 780 |
| tagggttat | tcggcggttg | gacgagatag | tggtgaatcg | tatcgcggcg ggggaagtta | 840 |
| tttagcggtt | agttaatgtt | attaaagaga | tgattgagaa | ttggtacgga gggagtcgag | 900 |

OLIGONUCLEOTIDE-IMMOBILIZED SUBSTRATE FOR DETECTING METHYLATION

RELATED APPLICATIONS

This application claims priority to JP Application No. 2002-292122, filed Oct. 4, 2002 which is incorporated herein by reference in its entirety.

FIELD OF THE INVENTION

The present invention relates to an oligonucleotide-immobilized substrate and method for detecting methylation of cytosine in DNA.

DESCRIPTION OF THE RELATED ART

Methylation of DNA plays an important role in regulation of replication and expression of DNA and so forth. In eucaryocytes, methylation of DNA is frequently occurs at the 5'-position of C (cytosine) present on the 5' side of G (guanine) (henceforth referred to as "CpG dinucleotide"). In particular, many CpG dinucleotides are found in promoter regions of many genes, and such a region is called CpG island (non-patent document 1). Although most of these CpG islands of autosome are generally methylated, CpG islands crowdedly exist in promoter regions are not methylated (non-patent document 2). It is also known that CpG islands in the promoter regions of P16 and P15, which are tumor suppressor genes, are methylated in leukemia or myeloma, and cancerization is caused by inactivation or change of expression amounts of these genes as a result of the methylation (non-patent document 3, 4).

Further, it is also reported that C located on the 5' side of a nucleotide other than G may also be methylated (non-patent document 5).

Furthermore, methylation is a modification scheme of DNA responsible for epigenetic change, and in genome imprinting, there is a mechanism for methylating either one of allelic genes for suppression of expression to suppress the expression so that a gene derived from one of parents should be expressed. Therefore, if the state of methylation is changed, there may be caused onsets of viviparous fatality, hereditary diseases and so forth (non-patent document 6, 7, 8).

Based on the above, it can be said that methylation of cytosine plays a significant role in control of gene expression, and change of the methylation pattern should cause diseases and so forth. Therefore, elucidation of the methylation pattern is important information for treatment and inference of prognosis of diseases.

Heretofore, for example, it has been considered that the presence or absence of methylation was different every CpG dinucleotide in CpG islands in the promoter region of a gene such as MGMT, hMLH1, or MRD1, considered to cause cellular cancerization (FIG. 1A). Therefore, for detecting the methylation through hybridization with capture oligonucleotides, the number of capture oligonucleotides to be used depends on the pattern of methylation. For this reason, capture oligonucleotides have been designed and synthesized in a complicated manner, while requiring an expensive device for detection.

As a method of detecting 5-methylcytosine, there is disclosed a method of detecting 5-methylcytosine that comprises treating chromosomal DNA with a chemical reagent whose reactivity on 5-methylcytosine is different from one on cytosine and hybridizing the chromosomal DNA with oligonucleotide, followed by a polymerase reaction, where the elongation of a nucleotide sequence depends on the state of methylation (patent document 1). In this method, the detection of 5-methylcytosine is performed one by one.

(patent document 1) WO 01/62064 A2
(non-patent document 1) Bird, A., Cell, 70, 5-8, 1992
(non-patent document 2) Ng, H-H. et al., Curr. Opin. Genet. Dev., 9, 158-163, 1999
(non-patent document 3) Shu-Xia Gao et al., Leukemia Res., 24, 39-46, 2000
(non-patent document 4) M. Gonzalez et al., Leukemia, 14, 183-187, 2000
(non-patent document 5) Gruenbaum, H., et al 1981. Nature 292:860-62
(non-patent document 6) Li, E., et al., Cell, 69, 915-926, 1992
(non-patent document 7) Okano, M., et al., Cell, 99, 247-257, 1999
(non-patent document 8) Xu, G-L., Nature, 402, 187-191, 1999.

SUMMARY OF THE INVENTION

An object of the present invention is to provide a method of detecting methylated cytosine in DNA in a simple manner and an oligonucleotide-immobilized substrate required for the detection.

The inventors of the present invention have made extensive studies for attaining the object and they have finally completed the present invention by finding out the following facts. That is, methylation of cytosine in a CpG island in a specific region does not vary from one CpG dinucleotide to another but CpG islands are divided into two, one with methylated cytosine in most of CpG dinucleotides and the other without methylated cytosine in most of CpG dinucleotides (FIGS. 1B and 1C). In addition, the presence or absence of methylation in CpG dinucleotides can be detected using two different types of oligonucleotides, one capable of detecting a nucleotide sequence being methylated in all the CpG dinucleotides and the other oligonucleotide capable of detecting a nucleotide sequence without being methylated.

That is, the present invention provides the followings.

(1) An oligonucleotide-immobilized substrate used for detecting presence or absence of methylation of C in a sample DNA, on which multiple kinds of capture oligonucleotides are immobilized, wherein the sample DNA contains a target sequence containing dinucleotides consisting of C that can be methylated and G on the 3' side of the C (henceforth referred to as "CpG dinucleotide") at a plurality of sites, the capture oligonucleotides include an oligonucleotide having a nucleotide sequence complimentary to or identical to a nucleotide sequence corresponding to the target sequence in which all of C's other than C's in the all of CpG dinucleotides are replaced with T's and an oligonucleotide having a nucleotide sequence complimentary to or identical to a nucleotide sequence corresponding to the target sequence in which all of C's are replaced with T's, and the presence or absence of methylation is detected based on hybridization of the sample DNA in which non-methylated C's have been converted into U's by deamination or an amplification product thereof and the capture oligonucleotides.

(2) The oligonucleotide-immobilized substrate according to (1), wherein the capture oligonucleotides are immobilized as dots on a base material, and each dot has an occupied area of 0.1 cm$^2$ or less.

(3) The oligonucleotide-immobilized substrate according to (1) or (2), wherein the capture oligonucleotides are oligonucleotides of 100-mer or less.

3

(4) The oligonucleotide-immobilized substrate according to any one of (1) to (3), wherein the capture oligonucleotides are immobilized via carbodiimide groups.
(5) A method for detecting presence or absence of methylation of C's in CpG dinucleotides in a sample DNA containing a target sequence containing CpG dinucleotides, wherein
multiple kinds of capture oligonucleotides immobilized on a base material and including an oligonucleotide having a nucleotide sequence complimentary to or identical to a nucleotide sequence corresponding to the target sequence in which all of C's other than C's in the all of CpG dinucleotide are replaced with T's and an oligonucleotide having a nucleotide sequence complimentary to or identical to a nucleotide sequence corresponding to the target sequence in which all of C's are replaced with T's are hybridized with the sample DNA in which non-methylated C's have been converted into U's by deamination or an amplification product thereof, and
the presence or absence of methylation is detected based on the result of the hybridization.
(6) The method according to claim 5, wherein the non-methylated C's have been deaminated by treatment with sodium bisulfite.

According to the present invention, methylated cytosine in DNA can be accurately detected in a simple manner without the need of numerous oligonucleotides.

BRIEF DESCRIPTION OF THE DRAWINGS

FIG. 1A shows a state in which the presence or absence of methylation varies from one CpG to another, FIG. 1B shows a state in which a plurality of adjacent CpG islands are being methylated or not, and FIG. 1C shows a state in which all of CpG islands are not methylated.

DETAILED DESCRIPTION OF THE INVENTION

Hereinafter, the present invention is explained in detail.

The oligonucleotide-immobilized substrate of the present invention is used in order to detect the presence or absence of methylation of C's in a sample DNA. The sample DNA includes a target sequence containing dinucleotides (CpG dinucleotides) each of which consists of C capable of being methylated and G on the 3' side of the C at a plurality of sites. The number of target sequences present in the sample DNA may be one or two or more.

The oligonucleotide-immobilized substrate comprises a base material and multiple kinds of capture oligonucleotides immobilized on the base material. The capture oligonucleotides include at least an oligonucleotide having a nucleotide sequence complimentary to or identical to a nucleotide sequence corresponding to the target sequence in which C's other than C's in CpG dinucleotides are replaced with T's (henceforth also referred to as "C-specific oligonucleotide") and an oligonucleotide having a nucleotide sequence complimentary to or identical to a nucleotide sequence corresponding to the target sequence in which all of C's are replaced with T's (henceforth also referred to as "T-specific oligonucleotide").

If such capture oligonucleotides as described above are allowed to hybridize with the sample DNA in which non-methylated cytosines are converted into uracils by deamination or an amplification product thereof, the C-specific oligonucleotide hybridizes to the target sequence, but the T-specific oligonucleotide does not hybridize thereto. That is, if C's in CpG dinucleotides are methylated, these C's are not converted into uracils, but C's other than C's in CpG dinucleotides are converted into uracils. On the other hand, if C's of CpG dinucleotides in the target sequence are not methylated, all of C's including those C's of CpG dinucleotides are converted into uracils. Therefore, the C-specific oligonucleotide does not hybridize to the target sequence, but the T-specific oligonucleotide hybridizes thereto. Thus, presence or absence of methylation of C's in CpG dinucleotides can be detected based on the result of the aforementioned hybridization.

Furthermore, in the present invention, methylation of CpG dinucleotides in a CpG island is not individually detected, and methylation of a plurality of adjacent CpG dinucleotides can be collectively detected.

Figure 1:
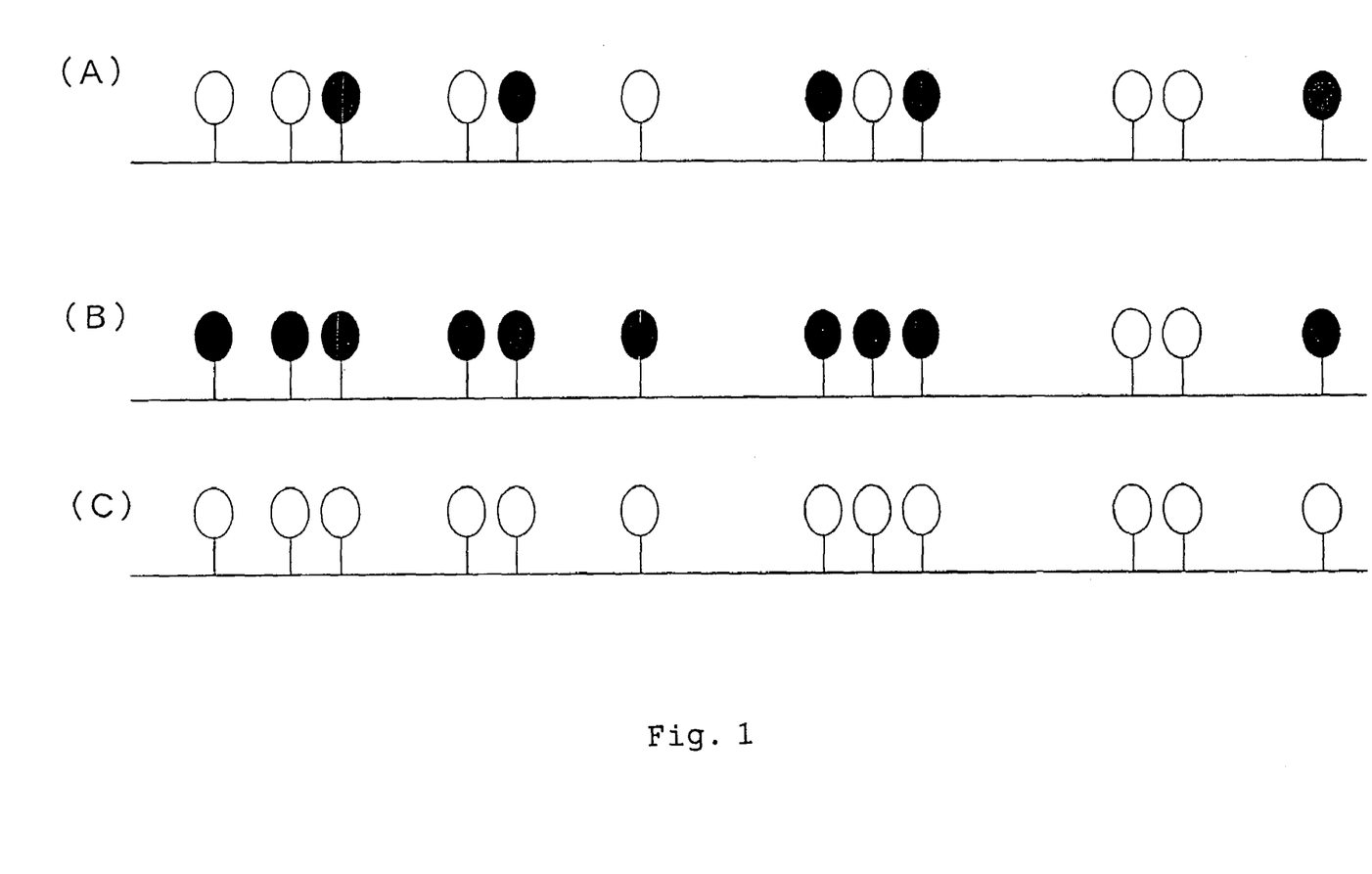
FIG. 1 is a diagram for illustrating a model for the methylation in CpG dinucleotides, where a closed circle represents a state in which C's in CpG dinucleotide are methylated and an open circle represents a state in which C's in CpG dinucleotide are not methylated.

FIG. 1 illustrates models of states of methylation. FIG. 1A shows a state in which the presence or absence of methylation varies from one CpG to another, FIG. 1B shows a state in which a plurality of adjacent CpG islands are being methylated or not, and FIG. 1C shows a state in which all of CpG islands are not methylated. In this model, capture oligonucleotides are designed such that the capture oligonucleotides correspond to a plurality of adjacent CpG islands among CpG islands shown in FIG. 1B to be methylated. As a result, there are two or more different bases between a C-specific oligonucleotide and a T-specific oligonucleotide, thereby enabling a more sensitive and precise detection, compared with the case where substitution of only one base is detected.

The sample DNA targeted for the detection of methylation according to the present invention is preferably human DNA. In addition, the target sequence is not limited to a particular one as far as it is a region to be methylated. Examples of the target sequence include carcinogenesis-related genes such as MGMT, hMLH1, MRD1, MINT31, CACNA1G, DCC, P16, MINT1, MINT2, COX2, p16, p14, p15, APC, RASSF1A, THBS1, COX2, MLH1, MGMT, GSTP1, DAPK, SOCS3, RUNX3, E-CADHERIN, CACNA1G and CHFR genes. Particularly preferable are promoter regions of these genes.

The sample DNA may be a single-stranded DNA or a double-stranded DNA. When the sample DNA is a single-stranded DNA, the capture oligonucleotides comprises an oligonucleotide having a nucleotide sequence complementary to a nucleotide sequence of target sequence in which C's other than C's of CpG dinucleotides are replaced with T's and an oligonucleotide having a nucleotide sequence complementary to a nucleotide sequence of target sequence in which all of C's are replaced with T's. When the sample DNA is a double-stranded DNA, the capture oligonucleotides comprises a strand containing a target sequence and a strand complementary thereto, and since CpG dinucleotides are symmetrically present in each strand, the capture oligonucleotides may be the same oligonucleotides as those in the case of single-stranded DNA or oligonucleotides having nucleotide sequences complementary thereto.

Although sequence and length of the capture oligonucleotides are not particularly limited so long as difference of a plurality of nucleotides can be detected by hybridization, the capture oligonucleotides usually have a length of preferably 10- to 100-mer, more preferably 10- to 25-mer, particularly preferably 13- to 25-mer.

Oligonucleotides used as the capture oligonucleotides can be chemically synthesized by a usual solid-phase synthesis method. The aforementioned capture oligonucleotides are immobilized on a substrate. At least one pair of capture oligonucleotides corresponding to one target sequence (T-specific oligonucleotide and C-specific oligonucleotide) are immobilized, and two or more of capture oligonucleotide pairs corresponding to two or more target sequences may be immobilized on a substrate.

Each oligonucleotide is preferably immobilized at a 5' end portion or 3' end portion on a base material. The base material used for the present invention is not particularly limited so long as it can immobilize oligonucleotides by physical adsorption or chemical bonding and bear usual hybridization conditions. Specifically, there can be mentioned those insoluble in solvents used for immobilization and hybridization of oligonucleotides etc. and being in the form of solid or gel at an ordinary temperature or within a temperature range around it (e.g., 0° C. to 100° C.). The expression that "a base material is insoluble in a solvent" means that, after a substance having a property of bonding to oligonucleotides such as carbodiimide group is carried on the base material and oligonucleotides are immobilized on the base material as described later, the base material is substantially insoluble in various solvents including aqueous solvents and organic solvents used in various process steps when it is used as, for example, DNA chip.

Specific examples of the material of such a base material include plastics, inorganic polymers, metals, natural polymers, ceramics and so forth.

Specific examples of the plastics include polyethylene, polystyrene, polycarbonate, polypropylene, polyamide, phenol resin, epoxy resin, polycarbodiimide resin, polyvinyl chloride, polyvinylidene fluoride, polyethylene fluoride, polyimide, acrylic resin and so forth.

Specific examples of the inorganic polymers include glass, quartz crystal, carbon, silica gel, graphite and so forth.

Specific examples of the metals include gold, platinum, silver, copper, iron, aluminum, magnet, paramagnet, apatite and so forth.

Examples of the natural polymers include polyamino acids, cellulose, chitin, chitosan, alginic acid and derivatives thereof.

Specific examples of the ceramics include alumina, silica, silicon carbide, silicon nitride, boron carbide and so forth.

Examples of shape of the aforementioned base materials include, for example, film, plate, particle, molded parts (bead, strip, well of multi-well plate, strip, tube, mesh, continuous foam, membrane, paper, needle, fiber, plate, slide, cell culture vessel etc.), latex and so forth. Sizes of these are not particularly limited.

When oligonucleotides are immobilized on the base material, the oligonucleotides may be immobilized directly on the base material, or a carrier may be carried on the base material and the oligonucleotides may be immobilized on the base material via the carrier. The base material itself may have a property of bonding to the oligonucleotides, or it may be one that can immobilize the oligonucleotides via a ligand having a property of bonding to oligonucleotides. The term "carry" used herein means that the oligonucleotides do not substantially dissociate from the base material in various solvents including aqueous solvents and organic solvents used when the oligonucleotides are immobilized on the base material, the oligonucleotide-immobilized base material is used as a DNA chip and so forth.

The carrier used for the present invention may be carried by utilizing only physical adhesion or it may be chemically carried via a covalent bond or the like so long as it is carried on the aforementioned base material. Further, the carrier may be carried on the entire surface of the base material or a part thereof, as required.

Examples of the carrier include low molecular weight organic molecules, plastics, inorganic polymers, metals, natural polymers, ceramics and so forth.

Specific examples of the low molecular weight organic molecules include carbodiimide group-containing compounds, isocyanate group-containing compounds, nitrogen yperite group-containing compounds, aldehyde group-containing compounds, amino group-containing compounds and so forth.

Specific examples of the plastics include polyethylene, polystyrene, polycarbonate, polypropylene, polyamide, phenol resin, epoxy resin, polycarbodiimide resin, polyvinyl chloride, polyvinylidene fluoride, polyethylene fluoride, polyimide, acrylic resin and so forth.

Specific examples of the inorganic polymers include glass, quartz crystal, carbon, silica gel, graphite and so forth.

Specific examples of the metals include gold, platinum, silver, copper, iron, aluminum, magnet, paramagnet, apatite and so forth.

Examples of the natural polymers include polyamino acids, cellulose, chitin, chitosan, alginic acid and derivatives thereof.

Specific examples of the ceramics include alumina, silica, silicon carbide, silicon nitride, boron carbide and so forth.

Such a carrier has a highly adhesive property to the aforementioned base material, and it is adhered to the base material by utilizing this adhesive property. A typical shape of the carrier in the case where it is carried on the base material by utilizing physical adhesion property is a coated film. As the method of providing the carrier as a coated film carried on the base material, there can be used known methods such as coating using spraying, dipping, brushing, stamp, vaporization, film coater and so forth.

For example, in order to provide a resin having carbodiimide groups carried on the whole surface of glass base material, a glass base material is first immersed in a solution obtained by dissolving an amino-substituted organoalkoxysilane such as 3-aminopropyltriethoxysilane in a suitable solvent under a temperature condition of 70 to 80° C. for about 2 to 3 hours, then the base material is taken out, and after the solution is washed out, the base material is dried by heating under a temperature condition of 100 to 120° C. for about 4 to 5 hours. After the drying, the base material can be immersed into an appropriate solvent, and the solvent can be added with a carbodiimide resin and stirred for washing under a temperature condition of 30 to 170° C. for about 12 hours. Further, it is also possible to allow the amino group of the 3-aminopropyltriethoxysilane and a functional group of nitrogen yperite group other than the oligonucleotide binding group to react by using an appropriate solvent to introduce the nitrogen yperite group on the surface of glass base material.

Introduction of various functional groups onto surfaces of such materials as described above has conventionally and generally been used, and methods therefor are known. Therefore, as also for cases where functional groups other than amino group are allowed to exist on a glass base material or the base material consists of a material other than glass, functional groups can be introduced onto the base material surface by using such known techniques.

Furthermore, some plastic base materials among those mentioned above properly have such functional groups as mentioned above. In such a case, the materials can be used as they are for the production of the base material without introducing functional groups onto surfaces thereof. Further, even such plastic base materials may be further introduced with functional groups and used for the production of the base material.

The capture oligonucleotides are immobilized on such a base material as described above at a 5' end portion or 3' end portion. The method for immobilizing oligonucleotides can suitably determined according to types of base material, functional groups on the surface of the base material, ligand and so forth.

The capture oligonucleotides may be bonded with a homopolymer consisting of three or more nucleotides on the side of an end to be immobilized on the base material. When a base material having carbodiimide groups on the surface is used, in particular, the oligonucleotides having such a homopolymer are firmly immobilized on the base material.

A known method can be used as the method of bonding such a homopolymer to ends of the oligonucleotides. For example, there can be specifically mentioned a method of synthesizing an oligonucleotide so that three or more nucleotides should be polymerized as an integral part of the oligonucleotide by using a commercially available nucleic acid synthesizer. There can also mentioned a method of binding a homopolymer to an oligonucleotide by using a chemical or enzymatic technique and so forth. The nucleobases constituting the homopolymer are selected from adenine, guanine, cytosine or thymine when the nucleic acid is DNA, or selected from adenine, guanine, cytosine or uracil when it is RNA.

The homopolymer preferably has a length of 3 to 100 nucleotides, more preferably 5 to 50 nucleotides, particularly preferably 10 to 40 nucleotides. If the number of nucleotide is 2 or less, a sufficient amount of nucleic acid cannot be immobilized on the base material. If the number of nucleotides is 101 or more, yield is markedly reduced in the nucleic acid production process.

The homopolymer may be formed from a homopolymer consisting of a certain kind of nucleotides and another homopolymer consisting of another kind of nucleotides ligated together.

Further, the 5' end of the nucleotide may be immobilized via an amino linker.

The oligonucleotides are preferably immobilized in dot-like areas. To immobilize in dot-like areas means that the areas on which the oligonucleotides are immobilized have a size sufficiently smaller than the size of the base material in such a degree that a plurality of the oligonucleotide-immobilized sites can be provided on the base material. Although shape of the dots is not particularly limited, it is generally preferably a circular shape. The oligonucleotides are usually immobilized on a plurality of sites on the base material, and the oligonucleotide-immobilized substrate is prepared as a so-called DNA array or DNA chip.

Specifically, the oligonucleotides are usually provided, for example, so as to be contained in water or a buffer so that activities of the oligonucleotides to be immobilized should be maintained during contact of the oligonucleotide and the base material for reaction. Temperature for the contact is preferably about 0 to 100° C. so that the activities of the oligonucleotides should not be degraded.

The immobilization can also be attained by irradiation of electromagnetic waves such as UV rays after the contact of the oligonucleotides and the base material. Further, the immobilization can also be attained by contacting a mixture of the oligonucleotides and a known compound such as carbodiimide resin, nitrogen yperite, polyamino acids and nitrocellulose, which are chemically bonded or physically associated, with the base material. Even in such a case, the immobilization can also be attained by irradiation of electromagnetic waves such as UV rays.

In the present invention, means for providing oligonucleotides, usually in the form of water or buffer containing the oligonucleotides, in dot-like areas on the base material includes a method of utilizing a dispenser, method of utilizing a pin, method of utilizing bubble jet and so forth. However, the present invention is not limited to these. Such apparatuses for providing solutions in small amounts are commercially available, and they can be used for the present invention.

The capture oligonucleotide-immobilized base material is preferably brought into contact with an excessive amount of bovine serum albumin (BSA), casein, salmon sperm DNA or the like to block unreacted portions after the capture oligonucleotides are immobilized on the base material in dot-like areas as described above in order to prevent non-specific binding of sample DNA.

In the present invention, the sample or amplification product thereof is hybridized with the capture oligonucleotides by using the aforementioned capture oligonucleotide-immobilized substrate.

The sample DNA is not particularly limited so long as it contains CpG dinucleotides and presence of methylation of C is expected for it, and DNA of various organisms may be used depending on the purpose. The sample DNA is prepared from microbial cell, various tissues of animals or plants. The sample DNA can be prepared in the same manner as usual preparation of DNA from cells. Further, although DNA prepared from cells can also be used as it is as the sample DNA, DNA of which target sequence or a region including the target sequence is amplified by PCR method or the like may also be used.

In the conventional methylation-specific PCR, at least three kinds of primers are required for one CpG. However, according to the present invention, a region containing multiple CpG's can be amplified with two kinds of primers. Further, in the methylation-specific PCR, a primer is designed so that its 3' end should correspond to cytosine of CpG. Therefore, when many CpG dinucleotides exist as in CpG island, methylation of CpG can be detected only for a relatively narrow region. On the other hand, according to the present invention, a primer may be designed so that C of CpG should not correspond to the 3' end, and thus PCR amplification is possible irrespective of methylation of C in CpG.

As for the sample DNA or its amplification product, C's not methylated are converted into uracils by deamination prior to the hybridization. This deamination of non-methylated C's can be performed by treating the sample DNA with bisulfite such as sodium bisulfite. Specifically, a solution containing the sample DNA is added with sodium bisulfite (pH 5) at a concentration of 2.5 M to 3.0 M and heated at 50° C. for 16 hours (J. G. Herman et al., Proc. Natl. Acad. Sci. USA, 93, 9821-9826, 1996). After the reaction with heating, the sample DNA is adsorbed on a silica-based filter for purification to remove the sodium bisulfite. After the removal, the sample DNA is collected from the silica-based filter and concentrated by ethanol precipitation or the like.

Although specific procedure of the hybridization is not particularly limited, it can be performed by, for example, immersing a substrate on which the capture oligonucleotides are immobilized in a solution containing the sample DNA, or spotting a solution containing the sample DNA onto areas where the capture oligonucleotides are immobilized. Further, areas where the capture oligonucleotides are immobilized may be covered with frames so that the frames should include the areas, and a solution containing the sample DNA may be poured into the frames.

The solution is not particularly limited so long as it allows hybridization of DNA, and various buffers can be used for it. For example, Tris-HCl having pH of about 6.5 to 8 can be mentioned. Usually, the solution is heated to a temperature at which base pairs formed in molecules of DNA or oligonucleotides dissociate, e.g., 90 to 100° C., and then adjusted to a temperature at which the capture oligonucleotides and a target sequence in the sample nucleic acid anneal. Specifically, this temperature is preferably 5 to 80° C. in general, although it depends on length of the capture oligonucleotides.

Although the method for detecting the hybridization is not particularly limited, it can be detected by, for example, labeling the sample nucleic acid with a labeling substance beforehand and detecting the label after the hybridization and washing of the substrate. Although the labeling substance is not particularly limited, examples thereof include substances usually used for detection of hybridization, for example, radioisotopes, fluorescent dyes, biotin, haptens, antigens and so forth. When biotin is used as a labeling substance, for example, a conjugate of a protein specifically binding to biotin (avidin or streptoavidin) and an enzyme chemically bonded to biotin can be bound after the hybridization operation, and a reaction can be performed by adding a compound that is degraded with the enzyme to form a dye that can deposit to readily detect presence or absence and location of hybridization.

EXAMPLES

Hereinafter, the present invention will be explained more specifically with reference to the following examples. However, the present invention is not only applied on genes exemplified in these examples.

Example 1

<1> Synthesis of Oligonucleotides

According to conventional procedures, oligonucleotides having nucleotide sequences represented by SEQ ID NOS: 1-13 were synthesized using an oligonucleotide synthesizer (Perkin-Elmer Applied Biosystems). The 5' ends of the respective oligonucleotides represented by SEQ ID NOS: 3, 4, and 5 were biotinylated. These oligonucleotides were dissolved in a 1×TE buffer (10 mM Tris-HCl, pH 8/1 mM EDTA) to a concentration of 1 pmol/µl.

<2> Immobilization of Capture Oligonucleotides on Substrate

Three spots of each of the oligonucleotide solutions of SEQ NOS: 6-13 were respectively formed on predetermined positions on a slide glass coated with a polycarbodiimide resin prepared by the method described in Japanese Patent Laid-Open Publication No. 08-334509. Each spot was 0.5 µl in volume and about 1 mm in diameter. Then, the slide glass was placed in a drier and dried for 20 minutes at 42° C. Subsequently, using UV stratalinker 2,400 (manufactured by STRATAGENE, Inc.), the slide glass was irradiated with ultraviolet rays of 600 mJ/cm$^2$ including a ray with a wavelength of 280-nm. After that, the slide glass was washed in water while the slide glass was shaken for 30 minutes, followed by being dried.

On the other hand, as a control, a nucleic acid-free solution (1×TE buffer) was spotted on a slide glass and immobilization procedure was performed in a manner similar to that described above.

<3> Preparation of Nucleic Acid Probe (Modification of DNA in Biological Test Sample with Bisulfite and PCR Reaction)

PCR amplification was performed on a CpG site of the promoter region of a gene that encodes MGMT protein derived from each of affected cell and normal cell of the identical cancer patient diagnosed as colorectal cancer. A nucleotide sequence of this region is shown in SEQ ID NO: 14. In the sequence, "y" denotes "c" or "t".

Figure 2:
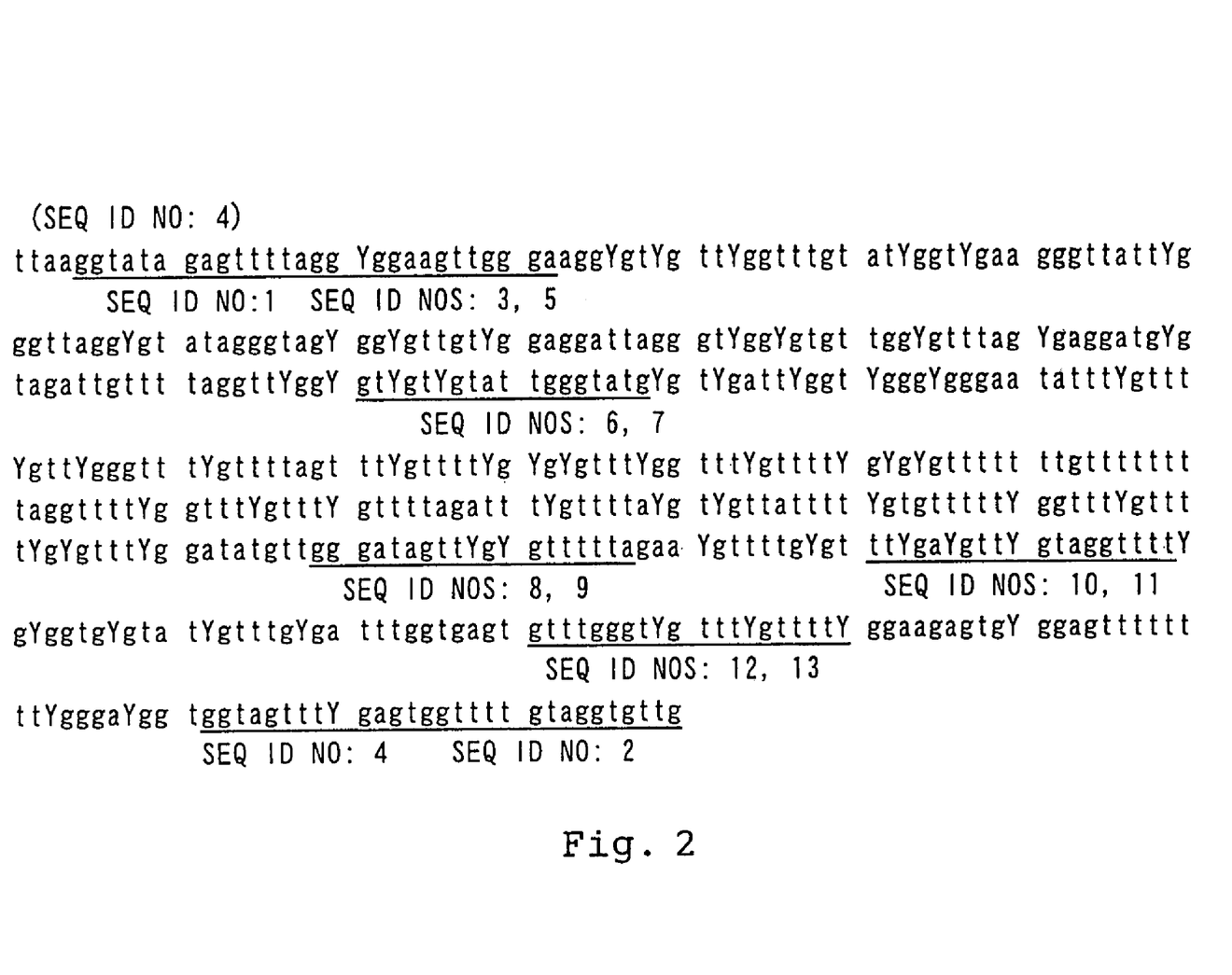
FIG. 2 illustrates a nucleotide sequence of a promoter region of a gene encoding a MGMT protein and corresponding positions of PCR primers and capture oligonucleotides. The full length sequence corresponds to SEQ ID NO: 14.

In addition, the nucleotide sequence and positions which correspond to each of the primers (SEQ ID NOS: 1-5) and capture oligonucleotides (SEQ ID NOS: 1-6) are shown in FIG. 2.

Each of the samples 1-10 was derived from the individual patient who had not received chemotherapy and radiotherapy before performing a surgical operation. The biological test sample was surgically removed from the patient at an operation, and immediately after that the biological test sample was then frozen and stored at –80° C.

DNA was extracted from each of the above biological samples by a conventional phenol/chloroform method. Then, 100 ng of the resulting DNA was modified for non-methylated cytosine with sodium bisulfite using a DNA modification kit (CpGenome, Intergen).

Subsequently, the DNA modified with sodium bisulfite was provided as a template and then PCR amplification was performed on the template using PCR primers represented by SEQ ID NOS: 1 and 2. Furthermore, 1 µL of the resulting PCR product was provided as a template and then PCR amplification was performed on the template using PCR primers represented by each of SEQ ID NOS: 3 and 4 (gene derived from a cancer cell was used as a template) or SEQ ID NOS: 4 and 5 (gene derived from a normal cell was used as a template). The number of nucleotides in the resulting PCR product was analyzed through agarose electrophoresis and ethidium bromide stain, resulting in about 500 bp for each of the samples 1-10 derived from cancer and normal cells. The resulting nucleic acid probe was labeled with biotin.

<4> Hybridization

10 µl of a hybridization solution (Arrayit UniHyb, Telechem International, Inc.) containing the nucleic acid probe (about 500 bp) of the sample 1 derived from cancer and normal cells was applied on the area where the nucleic acid has been immobilized on the slide glass. Subsequently, the slide glass was placed in a case (Hybrid Cassette, Telechem International Inc.) to prevent the slide glass from being immersed in water. Then, the case containing the slide glass was immersed in a water bath, followed by heating at 45° C. for 1 hour.

<5> Post Hybridization

After the above hybridization, using 2×SSC, the slide glass was subjected to post-hybridization washing once for one minute at room temperature to remove probes that non-specifically adsorbed on the oligonucleotide-immobilized slide glass.

<6> Detection of Immobilized Oligonucleotide and Hybridization 1.5 ml of a blocking solution (Block Ace, manufactured by Snow Brand Milk Products, Co., Ltd.) containing milk proteins was applied on the area of the slide glass where the hybridization solution was applied, and was then subjected to a blocking reaction for 30 minutes at room temperature. After the blocking solution was removed, 1.5 ml of a streptoavidin-alkaline phosphatase conjugate solution (manufactured by Vector Laboratories, Inc.) was applied on the above slide glass to allow a reaction for 30 minutes at room temperature.

Subsequently, the slide glass was immersed in a TBST solution (50 mM Tris-HCl (pH 7.5), 0.15 M NaCl, 0.05% Tween 20) and shaken for five minutes to remove non-reacted conjugates. At last, 1.5 ml of a substrate solution (TMB) was applied on the area of the slide glass on which the hybridization solution was applied and was then left stand for 30 minutes to perform a coloring reaction.

The results are shown in Table 1. Oligomers represented by SEQ ID NOS: 6, 8, 10, and 12 are complementary with DNA derived from a cancer cell. On the other hand, oligomers represented by SEQ ID NOS: 7, 9, 11, and 13 are complementary with DNA derived from a normal cell.

TABLE 1

Hybridization Signals (Sample 1)

| | DNA derived from cancer cell | DNA derived from normal cell |
|---|---|---|
| SEQ ID NO: 6 | ⊚ | x |
| SEQ ID NO: 7 | x | ⊚ |
| SEQ ID NO: 8 | ⊚ | x |
| SEQ ID NO: 9 | x | ⊚ |
| SEQ ID NO: 10 | ⊚ | x |
| SEQ ID NO: 11 | x | ⊚ |
| SEQ ID NO: 12 | ⊚ | x |
| SEQ ID NO: 13 | x | ⊚ |

⊚: Most signals emerged in extremely high sensitivity and extremely high clarity.
 : Most signals clearly emerged in high sensitivity and high clarity.
 : Some signals emerged in low sensitivity or unclearly.
x: Most signals emerged in low sensitivity or unclearly, or no signal emerged at all.

As was apparent from the results in Table 1, the DNA derived from the cancer cell and the DNA derived from the normal cell could be clearly distinguished by detecting a sequence having two or more nucleotide different from those of another sequence.

Example 2

<1> Oligonucleotide Synthesis

According to conventional procedures, oligonucleotides having nucleotide sequences represented by SEQ ID NOS: 15-28 were synthesized using an oligonucleotide synthesizer (Perkin-Elmer Applied Biosystems). In addition, the 5' ends of the respective oligonucleotides represented by SEQ ID NOS: 15 and 16 were biotinylated. These oligonucleotides were dissolved in a 1×TE buffer (10 mM Tris-HCl, pH 8/1 mM EDTA) to a concentration of 1 pmol/μl.

<2> Immobilization of Capture Oligonucleotides on Substrate

In the same manner as in Example 1, the oligonucleotides of SEQ ID NOS: 15-28 were immobilized on a slide glass coated with a polycarbodiimide resin.

On the other hand, as a control, a nucleic acid-free solution (1×TE buffer) was spotted on a slide glass and immobilization procedure was performed in the same manner as above.

<3> Preparation of Nucleic Acid Probe (Modification of DNA in Biological Test Sample with Bisulfite and PCR Reaction)

Figure 3:
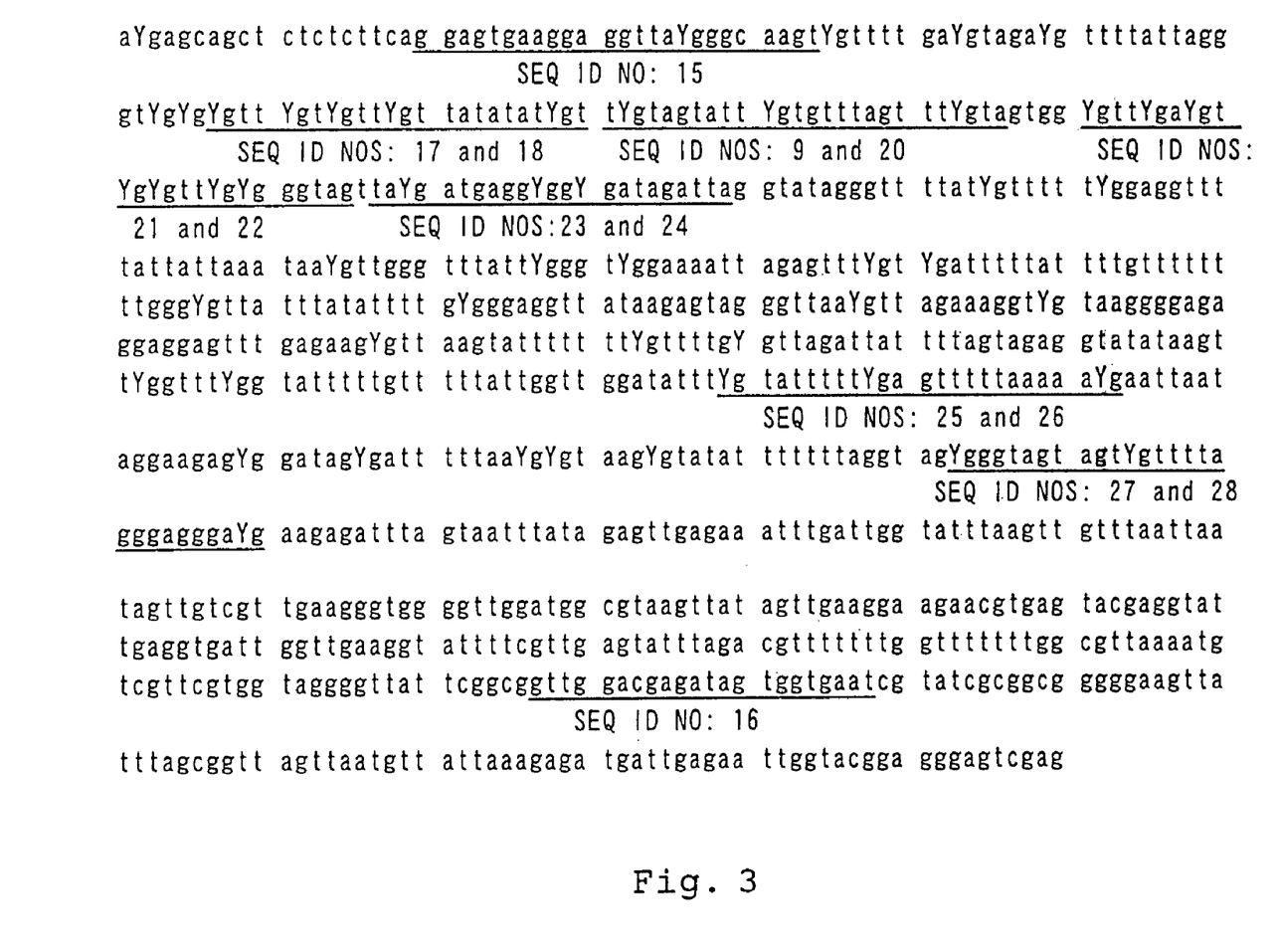
FIG. 3 illustrates a nucleotide sequence of a promoter region of a gene encoding a hMLH1 protein and corresponding positions of PCR primers and capture oligonucleotides. The full length sequence corresponds to SEQ ID NO: 29.

PCR amplification was performed on a CpG site of the promoter region of a gene that encodes hMLH1 protein derived from each of affected cell and normal cell of the identical cancer patient diagnosed as colorectal cancer. A nucleotide sequence of this site is represented as SEQ ID NO: 29. In the sequence, "y" denotes "c" or "t". In addition, the nucleotide sequence and positions which correspond to each of the primers (SEQ ID NOS: 15 and 16) and capture oligonucleotides (SEQ ID NOS: 17-28) are shown in FIG. 3.

Each of the samples 11 and 12 was derived from the individual patient who had not received chemotherapy and radiotherapy before performing a surgical operation. The biological test sample was surgically removed from the patient at an operation, and immediately after that the biological test sample was then frozen and stored at −80° C.

DNA was extracted from the above biological sample by a conventional phenol/chloroform method. Then, 100 ng of the resulting DNA was modified for non-methylated cytosine with sodium bisulfite using a DNA modification kit (CpGenome, Intergen).

Subsequently, the DNA modified with sodium bisulfite was provided as a template, and then PCR amplification was performed on the template using each of PCR primers represented by SEQ ID NOS: 15 and 16. The number of nucleotides in the resulting PCR product was analyzed through agarose electrophoresis and ethidium bromide stain, resulting in about 780 bp for each of the samples 11 and 12 derived from cancer and normal cells. The resulting nucleic acid probe was labeled with biotin.

<4> Hybridization

20 μl of a hybridization solution (Arrayit UniHyb, Telechem International, Inc.) containing the nucleic acid probe (about 780 bp) of the sample 11 derived from cancer and normal cells was applied on the area where the nucleic acid was immobilized on the slide glass. Subsequently, the slide glass was placed in a case (Hybrid Cassette, Telechem International Inc.) to prevent the slide glass from being immersed in water. Then, the case containing the slide glass was immersed in a water bath, followed by heating at 55° C. for 2 hours.

<5> Post Hybridization, Detection of Immobilized Oligonucleotide and Hybridization In the same manner as in Example 1, post hybridization, and the detection of immobilized oligonucleotide and hybridization were performed.

The results are shown in Table 2. Oligomers represented by SEQ ID NO: 17, SEQ ID NO: 19, SEQ ID NO: 21, SEQ ID NO: 23, SEQ ID NO: 25, and SEQ ID NO: 27 were complementary with DNA derived from a cancer cell. On the other hand, oligomers represented by SEQ ID NO: 18, SEQ ID NO: 20, SEQ ID NO: 22, SEQ ID NO: 24, SEQ ID NO: 26, and SEQ ID NO: 28 were complementary with DNA derived from a normal cell.

TABLE 2

Hybridization Signals (Samples 11 and 12)

| | DNA derived from cancer cell | DNA derived from normal cell |
|---|---|---|
| SEQ ID NO: 17 | ⊚ | x |
| SEQ ID NO: 18 | x | ⊚ |
| SEQ ID NO: 19 | ⊚ | x |
| SEQ ID NO: 20 | x | ⊚ |
| SEQ ID NO: 21 | ⊚ | x |
| SEQ ID NO: 22 | x | ⊚ |
| SEQ ID NO: 23 | ⊚ | x |
| SEQ ID NO: 24 | x | ⊚ |
| SEQ ID NO: 25 | ⊚ | x |
| SEQ ID NO: 26 | x | ⊚ |
| SEQ ID NO: 27 | ⊚ | x |
| SEQ ID NO: 28 | x | ⊚ |

⊚: Most signals emerged in extremely high sensitivity and extremely high clarity.
 : Most signals clearly emerged in high sensitivity and high clarity.
 : Some signals emerged in low sensitivity or unclearly.
x: Most signals emerged in low sensitivity or unclearly, or no signal emerged at all.

As was apparent from the results in Table 2, the DNA derived from the cancer cell and the DNA derived from the normal cell could be clearly distinguished by detecting a sequence having two or more bases different from those of another sequence.

What is claimed is:

1. An oligonucleotide-immobilized substrate for detecting presence or absence of methylation of C in a sample DNA comprising a target sequence comprising a plurality of CpG dinucleotides, consisting of capture probes, said capture probes consisting of multiple pairs of capture oligonucleotides wherein the capture oligonucleotide pairs consist of (a) an oligonucleotide consisting of a nucleotide sequence complementary to or identical to a nucleotide sequence corresponding to the target sequence in which all of C's other than C's in all CpG dinucleotides (C that can be methylated and G on the 3' side of the C) are replaced with T's and comprising a plurality of CpG dinucleotides and (b) an oligonucleotide consisting of a nucleotide sequence complementary to or identical to a nucleotide sequence corresponding to the target sequence in which all of C's are replaced with T's immobilized thereon and comprising a plurality of CpG dinucleotides from said target sequence.

2. The oligonucleotide-immobilized substrate according to claim 1, wherein the capture oligonucleotides are immobilized as dots on a base material, and each dot has an occupied area of 0.1 cm$^2$ or less.

3. The oligonucleotide-immobilized substrate according to claim 2, wherein the capture oligonucleotides are oligonucleotides of 100-mer or less.

4. The oligonucleotide-immobilized substrate according to claim 1, wherein the capture oligonucleotides are oligonucleotides of 100-mer or less.

5. The oligonucleotide-immobilized substrate according to claim 1, wherein the capture oligonucleotides are immobilized via carbodiimide groups.

6. The oligonucleotide-immobilized substrate according to claim 1, wherein the capture oligonucleotides are immobilized directly on a base material.

7. A method for detecting presence or absence of methylation of C's in CpG dinucleotides in a sample DNA containing a target sequence containing CpG dinucleotides, comprising:

providing multiple pairs of capture oligonucleotides immobilized on the oligonucleotide-immobilized substrate according to claim 1;

converting C's in the sample DNA into U's by deamination;

hybridizing the capture oligonucleotides with the deaminated sample DNA or an amplification product thereof, and detecting the presence or absence of methylation based on the result of the hybridization.

8. The method according to claim 7, wherein the non-methylated C's have been deaminated by treatment with sodium bisulfite.

* * * * *

UNITED STATES PATENT AND TRADEMARK OFFICE
CERTIFICATE OF CORRECTION

| | | |
|---|---|---|
| PATENT NO. | : 7,238,518 B2 | Page 1 of 1 |
| APPLICATION NO. | : 10/677853 | |
| DATED | : July 3, 2007 | |
| INVENTOR(S) | : Matsubara et al. | |

It is certified that error appears in the above-identified patent and that said Letters Patent is hereby corrected as shown below:

Title Page, "Foreign Patent Documents," add --EP 1 312 685 5/2003--

Title Page, "Other Publications," "Nagasaka, et al. "CpG Island Microarray to Analyze Methylation of $O^8$ Methyiguarine-DNA Methyltransferase in Colon Cancer,"" should be changed to --Nagasaka, et al. "CpG Island Microarray to Analyze Methylation Profiles of $O^6$ Methylguanine-DNA Methyltransferase in Colon Cancer"--

Column 7, Line 22, "There can also mentioned" should be changed to --There can also be mentioned--

Signed and Sealed this

Eighth Day of January, 2008

JON W. DUDAS
*Director of the United States Patent and Trademark Office*